(12) United States Patent
Robertson et al.

(10) Patent No.: US 12,213,817 B2
(45) Date of Patent: Feb. 4, 2025

(54) SYSTEMS AND METHODS FOR RADIOGRAPHIC MONITORING OF SHUNTS

(71) Applicant: Shifamed Holdings, LLC, Campbell, CA (US)

(72) Inventors: Scott Robertson, Portland, OR (US); Brian Fahey, Menlo Park, CA (US); Miles Alexander, Fremont, CA (US); Peter Andriola, Castro Valley, CA (US); William Jason Fox, San Mateo, CA (US); Anthony Pantages, San Jose, CA (US)

(73) Assignee: Shifamed Holdings, LLC, Campbell, CA (US)

( * ) Notice: Subject to any disclaimer, the term of this patent is extended or adjusted under 35 U.S.C. 154(b) by 2 days.

(21) Appl. No.: 17/919,491

(22) PCT Filed: Apr. 23, 2021

(86) PCT No.: PCT/US2021/028787
§ 371 (c)(1),
(2) Date: Oct. 17, 2022

(87) PCT Pub. No.: WO2021/216964
PCT Pub. Date: Oct. 28, 2021

(65) Prior Publication Data
US 2024/0000404 A1 Jan. 4, 2024

Related U.S. Application Data

(60) Provisional application No. 63/014,318, filed on Apr. 23, 2020.

(51) Int. Cl.
*A61B 6/00* (2024.01)
*A61B 6/12* (2006.01)
*A61B 6/50* (2024.01)

(52) U.S. Cl.
CPC ............. *A61B 6/12* (2013.01); *A61B 6/503* (2013.01); *A61B 6/5217* (2013.01); *A61B 6/5264* (2013.01)

(58) Field of Classification Search
CPC ..................................................... A61B 6/12
See application file for complete search history.

(56) References Cited

U.S. PATENT DOCUMENTS

| | | |
|---|---|---|
| 3,874,388 A | 4/1975 | King et al. |
| 4,601,309 A | 7/1986 | Chang |

(Continued)

FOREIGN PATENT DOCUMENTS

| | | |
|---|---|---|
| AU | 2005211243 | 8/2005 |
| AU | 2010344182 | 8/2012 |

(Continued)

OTHER PUBLICATIONS

Jodi Perkins, "Corvia Medical and physIQ Partner in Global Phase 3 Heart Failure Clinical Trial to Leverage Novel Digital Endpoints," Press Release, 2019 Copyright, Medical Alley Association, 3 pages.

(Continued)

*Primary Examiner* — Joseph M Santos Rodriguez
(74) *Attorney, Agent, or Firm* — Perkins Coie LLP (57) ABSTRACT

The present technology relates to interatrial shunting systems and methods. In some embodiments, the present technology includes a method for monitoring a shunting element implanted in a patient and having a lumen fluidly coupling cavities of the patient's heart. The method can comprise obtaining first and second radiographic images of at least two radiopaque elements associated with the lumen of the shunting element. A spatial relationship between the radiopaque elements varies according to a size of the lumen. The first radiographic image can be taken from a first viewing angle and the second radiographic image can be (Continued)

taken from a second viewing angle generally orthonormal to the first viewing angle. The method also includes determining the size of the lumen based, at least in part. on locations of the radiopaque elements in the first and second radiographic images.

22 Claims, 4 Drawing Sheets

(56) References Cited

U.S. PATENT DOCUMENTS

| | | |
|---|---|---|
| 4,662,355 A | 5/1987 | Pieronne et al. |
| 4,705,507 A | 11/1987 | Boyles |
| 4,836,204 A | 6/1989 | Landymore et al. |
| 4,979,955 A | 12/1990 | Smith |
| 4,995,857 A | 2/1991 | Arnold |
| 5,186,431 A | 2/1993 | Tamari |
| 5,267,940 A | 12/1993 | Moulder |
| 5,290,227 A | 3/1994 | Pasque |
| 5,312,341 A | 5/1994 | Turi |
| 5,326,374 A | 7/1994 | Ilbawi et al. |
| 5,332,402 A | 7/1994 | Teitelbaum |
| 5,334,217 A | 8/1994 | Das |
| 5,409,019 A | 4/1995 | Wilk |
| 5,429,144 A | 7/1995 | Wilk |
| 5,500,015 A | 3/1996 | Deac |
| 5,531,759 A | 7/1996 | Kensey et al. |
| 5,556,386 A | 9/1996 | Todd |
| 5,584,803 A | 12/1996 | Stevens et al. |
| 5,597,377 A | 1/1997 | Aldea |
| 5,645,559 A | 7/1997 | Hachtman et al. |
| 5,655,548 A | 8/1997 | Nelson et al. |
| 5,662,711 A | 9/1997 | Douglas |
| 5,702,412 A | 12/1997 | Popov et al. |
| 5,725,552 A | 3/1998 | Kotula et al. |
| 5,741,297 A | 4/1998 | Simon |
| 5,795,307 A | 8/1998 | Krueger |
| 5,810,836 A | 9/1998 | Hussein et al. |
| 5,824,071 A | 10/1998 | Nelson et al. |
| 5,916,193 A | 6/1999 | Stevens et al. |
| 5,941,850 A | 8/1999 | Shah et al. |
| 5,957,949 A | 9/1999 | Leonhardt et al. |
| 6,039,759 A | 3/2000 | Carpentier et al. |
| 6,077,298 A | 6/2000 | Tu et al. |
| 6,126,686 A | 10/2000 | Badylak et al. |
| 6,165,188 A | 12/2000 | Saadat et al. |
| 6,210,318 B1 | 4/2001 | Lederman |
| 6,217,541 B1 | 4/2001 | Yu |
| 6,242,762 B1 | 6/2001 | Brown et al. |
| 6,254,564 B1 | 7/2001 | Wilk et al. |
| 6,260,552 B1 | 7/2001 | Mortier et al. |
| 6,270,526 B1 | 8/2001 | Cox |
| 6,277,078 B1 | 8/2001 | Porat et al. |
| 6,302,892 B1 | 10/2001 | Wilk |
| 6,328,699 B1 | 12/2001 | Eigler et al. |
| 6,344,022 B1 | 2/2002 | Jarvik |
| 6,358,277 B1 | 3/2002 | Duran |
| 6,406,422 B1 | 6/2002 | Landesberg |
| 6,447,539 B1 | 9/2002 | Nelson et al. |
| 6,451,051 B2 | 9/2002 | Drasler et al. |
| 6,458,153 B1 | 10/2002 | Bailey et al. |
| 6,468,303 B1 | 10/2002 | Amplatz et al. |
| 6,478,776 B1 | 11/2002 | Rosenman et al. |
| 6,491,705 B2 | 12/2002 | Gifford, III et al. |
| 6,527,698 B1 | 3/2003 | Kung et al. |
| 6,544,208 B2 | 4/2003 | Ethier et al. |
| 6,562,066 B1 | 5/2003 | Martin |
| 6,572,652 B2 | 6/2003 | Shaknovich |
| 6,589,198 B1 | 7/2003 | Soltanpour et al. |
| 6,632,169 B2 | 10/2003 | Korakianitis et al. |
| 6,638,303 B1 | 10/2003 | Campbell |
| 6,641,610 B2 | 11/2003 | Wolf et al. |
| 6,652,578 B2 | 11/2003 | Bailey et al. |
| 6,685,664 B2 | 2/2004 | Levin et al. |
| 6,712,836 B1 | 3/2004 | Berg et al. |
| 6,911,043 B2 | 6/2005 | Myers et al. |
| 7,001,409 B2 | 2/2006 | Amplatz |
| 7,011,095 B2 | 3/2006 | Wolf et al. |
| 7,056,294 B2 | 6/2006 | Khairkhahan et al. |
| 7,149,587 B2 | 12/2006 | Wardle et al. |
| 7,175,656 B2 | 2/2007 | Khairkhahan |
| 7,270,675 B2 | 9/2007 | Chun et al. |
| 7,294,115 B1 | 11/2007 | Wilk |
| 7,311,690 B2 | 12/2007 | Burnett |
| 7,311,730 B2 | 12/2007 | Gabbay |
| 7,317,951 B2 | 1/2008 | Schneider et al. |
| 7,390,310 B2 | 6/2008 | McCusker et al. |
| 7,513,908 B2 | 4/2009 | Lattouf |
| 7,524,329 B2 | 4/2009 | Rucker |
| 7,524,330 B2 | 4/2009 | Berreklouw |
| 7,524,332 B2 | 4/2009 | Osborne et al. |
| 7,608,067 B2 | 10/2009 | Bonni |
| 7,699,059 B2 | 4/2010 | Fonseca et al. |
| 7,736,327 B2 | 6/2010 | Wilk et al. |
| 7,780,725 B2 | 8/2010 | Haug et al. |
| 7,794,473 B2 | 9/2010 | Tessmer et al. |
| 7,806,921 B2 | 10/2010 | Hoffman |
| 7,892,246 B2 | 2/2011 | Akin et al. |
| 7,905,901 B2 | 3/2011 | Corcoran et al. |
| 7,922,764 B2 | 4/2011 | Gordy et al. |
| 7,938,840 B2 | 5/2011 | Golden et al. |
| 7,967,769 B2 | 6/2011 | Faul et al. |
| 7,988,724 B2 | 8/2011 | Salahieh et al. |
| 8,012,198 B2 | 9/2011 | Hill et al. |
| 8,016,877 B2 | 9/2011 | Seguin et al. |
| 8,043,360 B2 | 10/2011 | McNamara et al. |
| 8,070,708 B2 | 12/2011 | Rottenberg et al. |
| 8,091,556 B2 | 1/2012 | Keren et al. |
| 8,096,959 B2 | 1/2012 | Stewart et al. |
| 8,147,545 B2 | 4/2012 | Avior |
| 8,157,860 B2 | 4/2012 | McNamara et al. |
| 8,172,896 B2 | 5/2012 | McNamara et al. |
| 8,235,916 B2 | 8/2012 | Whiting et al. |
| 8,235,933 B2 | 8/2012 | Keren et al. |
| 8,246,677 B2 | 8/2012 | Ryan |
| 8,252,042 B2 | 8/2012 | McNamara et al. |
| 8,303,511 B2 | 11/2012 | Eigler et al. |
| 8,348,996 B2 | 1/2013 | Tuval et al. |
| 8,398,708 B2 | 3/2013 | Meiri et al. |
| 8,460,366 B2 | 6/2013 | Rowe |
| 8,460,372 B2 | 6/2013 | McNamara et al. |
| 8,597,225 B2 | 12/2013 | Kapadia |
| 8,647,381 B2 | 2/2014 | Essinger et al. |
| 8,696,611 B2 | 4/2014 | Nitzan et al. |
| 8,740,962 B2 | 6/2014 | Finch et al. |
| 8,745,845 B2 | 6/2014 | Finch et al. |
| 8,747,458 B2 | 6/2014 | Tuval et al. |
| 8,752,258 B2 | 6/2014 | Finch et al. |
| 8,764,848 B2 | 7/2014 | Callaghan et al. |
| 8,882,697 B2 | 11/2014 | Celermajer et al. |
| 8,951,223 B2 | 2/2015 | McNamara et al. |
| 9,005,155 B2 | 4/2015 | Sugimoto |
| 9,034,034 B2 | 5/2015 | Nitzan et al. |
| 9,138,213 B2 | 9/2015 | Amin et al. |
| 9,205,236 B2 | 12/2015 | McNamara et al. |
| 9,232,997 B2 | 1/2016 | Sugimoto et al. |
| 9,277,995 B2 | 3/2016 | Celermajer et al. |
| 9,358,371 B2 | 6/2016 | McNamara et al. |
| 9,456,812 B2 | 10/2016 | Finch et al. |
| 9,629,715 B2 | 4/2017 | Nitzan et al. |
| 9,642,993 B2 | 5/2017 | McNamara et al. |
| 9,649,480 B2 | 5/2017 | Sugimoto et al. |
| 9,681,948 B2 | 6/2017 | Levi et al. |
| 9,707,382 B2 | 7/2017 | Nitzan et al. |
| 9,713,696 B2 | 7/2017 | Yacoby et al. |
| 9,724,499 B2 | 8/2017 | Rottenberg et al. |
| 9,757,107 B2 | 9/2017 | McNamara et al. |
| 9,775,636 B2 | 10/2017 | Fazio et al. |
| 9,918,856 B2 | 3/2018 | Favier et al. |
| 9,937,036 B2 | 4/2018 | Sugimoto et al. |
| 9,943,670 B2 | 4/2018 | Keren et al. |
| 9,980,815 B2 | 5/2018 | Nitzan et al. |
| 10,045,766 B2 | 8/2018 | McNamara et al. |

(56) References Cited

U.S. PATENT DOCUMENTS

| | | |
|---|---|---|
| 10,076,403 B1 | 9/2018 | Eigler et al. |
| 10,188,375 B2 | 1/2019 | McNamara et al. |
| 10,207,087 B2 | 2/2019 | Keren |
| 10,251,740 B2 | 4/2019 | Eigler et al. |
| 10,292,690 B2 | 5/2019 | Celermajer et al. |
| 10,350,384 B2 | 7/2019 | Farnan et al. |
| 10,357,357 B2 | 7/2019 | Levi et al. |
| 10,368,981 B2 | 8/2019 | Nitzan et al. |
| 10,376,359 B2 | 8/2019 | Essinger et al. |
| 10,376,680 B2 | 8/2019 | McNamara et al. |
| 10,398,421 B2 | 9/2019 | Celermajer |
| 10,405,903 B1 | 9/2019 | Biesinger et al. |
| 10,413,284 B2 | 9/2019 | McNamara et al. |
| 10,413,286 B2 | 9/2019 | McNamara et al. |
| 10,463,477 B2 | 11/2019 | Forcucci et al. |
| 10,463,490 B2 | 11/2019 | Rottenberg et al. |
| 10,478,594 B2 | 11/2019 | Yacoby et al. |
| 10,568,751 B2 | 2/2020 | McNamara |
| 10,588,611 B2 | 3/2020 | Magnin et al. |
| 10,610,210 B2 | 4/2020 | Finch et al. |
| 10,624,621 B2 | 4/2020 | Celermajer |
| 10,632,292 B2 | 4/2020 | Forcucci et al. |
| 10,639,459 B2 | 5/2020 | Nitzan et al. |
| 10,675,450 B2 | 6/2020 | Finch |
| 10,828,151 B2 | 11/2020 | Nitzan et al. |
| 10,835,394 B2 | 11/2020 | Nae et al. |
| 10,898,698 B1 | 1/2021 | Eigler et al. |
| 10,912,645 B2 | 2/2021 | Rottenberg et al. |
| 10,925,706 B2 | 2/2021 | Eigler et al. |
| 10,932,786 B2 | 3/2021 | McNamara et al. |
| 10,940,296 B2 | 3/2021 | Keren |
| 10,945,716 B2 | 3/2021 | Chen et al. |
| 11,135,410 B2 | 10/2021 | Finch et al. |
| 11,633,194 B2 | 4/2023 | Alexander et al. |
| 2002/0169371 A1 | 11/2002 | Gilderdale |
| 2002/0169475 A1 | 11/2002 | Gainor et al. |
| 2002/0177891 A1 | 11/2002 | Miles et al. |
| 2003/0125798 A1 | 7/2003 | Martin |
| 2003/0127090 A1 | 7/2003 | Gifford et al. |
| 2004/0016514 A1 | 1/2004 | Nien |
| 2004/0077988 A1 | 4/2004 | Tweden et al. |
| 2004/0088045 A1 | 5/2004 | Cox |
| 2004/0093075 A1 | 5/2004 | Kuehne |
| 2004/0143294 A1 | 7/2004 | Corcoran et al. |
| 2004/0147869 A1 | 7/2004 | Wolf et al. |
| 2004/0162514 A1 | 8/2004 | Alferness et al. |
| 2004/0210190 A1 | 10/2004 | Kohler et al. |
| 2004/0215067 A1 | 10/2004 | Stiger et al. |
| 2004/0215323 A1 | 10/2004 | Stiger |
| 2005/0033351 A1 | 2/2005 | Newton |
| 2005/0148925 A1 | 7/2005 | Rottenberg et al. |
| 2005/0165344 A1 | 7/2005 | Dobak, III |
| 2005/0192627 A1 | 9/2005 | Whisenant et al. |
| 2006/0025857 A1 | 2/2006 | Bergheim et al. |
| 2006/0111660 A1 | 5/2006 | Wolf et al. |
| 2007/0010837 A1 | 1/2007 | Tanaka |
| 2007/0010852 A1 | 1/2007 | Blaeser et al. |
| 2007/0043435 A1 | 2/2007 | Seguin et al. |
| 2007/0213813 A1 | 9/2007 | Von Segesser et al. |
| 2007/0282157 A1 | 12/2007 | Rottenberg et al. |
| 2008/0119891 A1 | 5/2008 | Miles et al. |
| 2009/0243956 A1 | 10/2009 | Keilman et al. |
| 2009/0276040 A1 | 11/2009 | Rowe et al. |
| 2011/0054515 A1 | 3/2011 | Bridgeman et al. |
| 2011/0218480 A1 | 9/2011 | Rottenberg et al. |
| 2011/0218481 A1 | 9/2011 | Rottenberg et al. |
| 2011/0257723 A1 | 10/2011 | McNamara |
| 2011/0295183 A1 | 12/2011 | Finch et al. |
| 2012/0290062 A1 | 11/2012 | McNamara et al. |
| 2014/0128796 A1 | 5/2014 | Keren et al. |
| 2014/0163449 A1 | 6/2014 | Rottenberg et al. |
| 2014/0277054 A1 | 9/2014 | McNamara et al. |
| 2015/0034217 A1 | 2/2015 | Vad |
| 2015/0119796 A1 | 4/2015 | Finch |
| 2015/0141807 A1 | 5/2015 | Fetterly |
| 2015/0230843 A1 | 8/2015 | Palmer et al. |
| 2016/0151179 A1 | 6/2016 | Favier et al. |
| 2017/0340460 A1 | 11/2017 | Rosen et al. |
| 2018/0014828 A1 | 1/2018 | Fonte et al. |
| 2018/0256865 A1 | 9/2018 | Finch et al. |
| 2019/0021861 A1 | 1/2019 | Finch |
| 2019/0254814 A1 | 8/2019 | Nitzan et al. |
| 2019/0262118 A1 | 8/2019 | Eigler et al. |
| 2019/0269392 A1 | 9/2019 | Celermajer et al. |
| 2019/0328513 A1 | 10/2019 | Levi et al. |
| 2019/0336163 A1 | 11/2019 | McNamara et al. |
| 2020/0060825 A1 | 2/2020 | Rottenberg et al. |
| 2020/0078196 A1 | 3/2020 | Rosen et al. |
| 2020/0078558 A1 | 3/2020 | Yacoby et al. |
| 2020/0188143 A1 | 6/2020 | McNamara |
| 2020/0245991 A1 | 8/2020 | Celermajer |
| 2020/0261705 A1 | 8/2020 | Nitzan et al. |
| 2020/0268515 A1 | 8/2020 | Vettukattil et al. |
| 2020/0315599 A1 | 10/2020 | Nae et al. |
| 2020/0368505 A1 | 11/2020 | Nae et al. |
| 2021/0052378 A1 | 2/2021 | Nitzan et al. |
| 2021/0059527 A1 | 3/2021 | Najafi |
| 2021/0100665 A1 | 4/2021 | Nae et al. |
| 2021/0121179 A1 | 4/2021 | Ben-David et al. |
| 2021/0153776 A1 | 5/2021 | Minar et al. |
| 2021/0177508 A1 | 6/2021 | Kellerman |
| 2021/0259732 A1 | 8/2021 | Dicicco et al. |
| 2021/0259829 A1 | 8/2021 | Quinn |
| 2021/0259839 A1 | 8/2021 | Cole et al. |
| 2021/0290214 A1 | 9/2021 | Cole et al. |
| 2021/0299425 A1 | 9/2021 | Kume et al. |
| 2021/0299430 A1 | 9/2021 | Ratz et al. |
| 2021/0361257 A1 | 11/2021 | Eimer et al. |
| 2024/0032869 A1 | 2/2024 | Andriola et al. |

FOREIGN PATENT DOCUMENTS

| | | |
|---|---|---|
| AU | 2011332324 | 6/2013 |
| AU | 2012214279 | 8/2013 |
| AU | 2018228451 | 9/2019 |
| CA | 2785041 | 8/2011 |
| CA | 2786575 | 8/2011 |
| CA | 2818417 | 5/2012 |
| CA | 2955389 | 1/2016 |
| CA | 3054891 | 9/2018 |
| CN | 101415452 | 4/2009 |
| CN | 102458316 | 5/2012 |
| CN | 102905626 | 1/2013 |
| CN | 103458832 | 12/2013 |
| CN | 105662653 | 6/2016 |
| CN | 109646063 A | 4/2019 |
| CN | 110536657 | 12/2019 |
| EP | 2097012 | 9/2009 |
| EP | 2528646 | 12/2012 |
| EP | 2642954 | 10/2013 |
| EP | 2967867 | 1/2016 |
| EP | 3087953 | 11/2016 |
| EP | 3291773 | 3/2018 |
| EP | 3329860 | 6/2018 |
| EP | 3579907 | 12/2019 |
| EP | 3589238 | 1/2020 |
| EP | 3624701 | 3/2020 |
| EP | 2999412 | 5/2020 |
| EP | 3705154 | 9/2020 |
| EP | 3716877 | 10/2020 |
| EP | 3740163 | 11/2020 |
| EP | 3766431 | 1/2021 |
| EP | 3834737 | 6/2021 |
| EP | 3843618 | 7/2021 |
| EP | 3871626 | 9/2021 |
| EP | 3886761 | 10/2021 |
| EP | 3893731 | 10/2021 |
| EP | 3897369 | 10/2021 |
| IL | 176973 | 12/2006 |
| IL | 221127 | 9/2012 |
| IL | 226374 | 7/2013 |
| IL | 215975 | 11/2016 |
| IL | 227756 | 6/2017 |
| IL | 220201 | 8/2017 |

(56) References Cited

FOREIGN PATENT DOCUMENTS

| | | |
|---|---|---|
| IL | 253648 | 9/2017 |
| IL | 255379 | 12/2017 |
| IL | 252395 | 4/2020 |
| IN | 2011KN04472 | 7/2012 |
| IN | 2012KN01275 | 2/2013 |
| IN | 2013KN01954 | 11/2013 |
| IN | 2013CN06525 | 8/2014 |
| IN | 2012KN01988 | 8/2016 |
| JP | 2007527742 | 10/2007 |
| JP | 2010508093 | 3/2010 |
| JP | 2013046784 | 3/2013 |
| JP | 2014503246 | 2/2014 |
| JP | 2014512869 | 5/2014 |
| JP | 2020509812 | 4/2020 |
| KR | 20010046155 | 6/2001 |
| WO | WO2005074367 | 8/2005 |
| WO | WO2007083288 | 7/2007 |
| WO | WO2008055301 | 5/2008 |
| WO | WO2010128501 | 11/2010 |
| WO | WO2010129089 | 11/2010 |
| WO | WO2011093941 | 8/2011 |
| WO | WO2011094521 | 8/2011 |
| WO | WO2012071075 | 5/2012 |
| WO | WO2012085913 | 6/2012 |
| WO | WO2012109557 | 8/2012 |
| WO | WO2013014539 | 1/2013 |
| WO | WO2013096965 | 6/2013 |
| WO | WO2014150106 | 9/2014 |
| WO | WO2014188279 | 11/2014 |
| WO | WO2016014821 | 1/2016 |
| WO | WO2016038115 | 3/2016 |
| WO | WO2016178171 | 11/2016 |
| WO | WO2018158747 | 9/2018 |
| WO | WO2019142152 | 7/2019 |
| WO | WO2019179447 | 9/2019 |
| WO | WO2019188917 | 10/2019 |
| WO | WO2019189079 | 10/2019 |
| WO | WO2019209420 | 10/2019 |
| WO | WO2020094085 | 5/2020 |
| WO | WO2020094087 | 5/2020 |
| WO | WO2020094094 | 5/2020 |
| WO | WO2020110048 | 6/2020 |
| WO | WO2020123338 | 6/2020 |
| WO | WO2020202046 | 10/2020 |
| WO | WO2020215090 | 10/2020 |
| WO | WO2020217194 | 10/2020 |
| WO | WO2020219265 | 10/2020 |
| WO | WO2020225698 | 11/2020 |
| WO | WO2020225757 | 11/2020 |
| WO | WO2020229636 | 11/2020 |
| WO | WO2020234751 | 11/2020 |
| WO | WO2020251700 | 12/2020 |
| WO | WO2020259492 | 12/2020 |
| WO | WO2021025905 | 2/2021 |
| WO | WO2021026485 | 2/2021 |
| WO | WO2021046753 | 3/2021 |
| WO | WO2021055264 | 3/2021 |
| WO | WO2021065873 | 4/2021 |
| WO | WO2021065874 | 4/2021 |
| WO | WO2021065875 | 4/2021 |
| WO | WO2021065912 | 4/2021 |
| WO | WO2021086707 | 5/2021 |
| WO | WO2021091566 | 5/2021 |
| WO | WO2021096766 | 5/2021 |
| WO | WO2021101707 | 5/2021 |
| WO | WO2021113670 | 6/2021 |
| WO | WO2021136252 | 7/2021 |
| WO | WO2021136261 | 7/2021 |
| WO | WO2021138041 | 7/2021 |
| WO | WO2021146342 | 7/2021 |
| WO | WO2021158559 | 8/2021 |
| WO | WO2021162888 | 8/2021 |
| WO | WO2021178636 | 9/2021 |
| WO | WO2021190547 | 9/2021 |
| WO | WO2021212011 | 10/2021 |
| WO | WO2021224736 | 11/2021 |
| WO | WO2022093918 | 5/2022 |

OTHER PUBLICATIONS

Lehner et al., "The Creation of an Interatrial Right-To-Left Shunt in Patients with Severe, Irreversible Pulmonary Hypertension: Rationale, Devices, Outcomes," Current Cardiology Reports (2019) 21: 31, https://doi.org/10.1007/s11886-019-1118-8; 9 pages.

International Search Report and Written Opinion received for International Application No. PCT/US21/28787, filed Apr. 23, 2021; Applicant: Shifamed Holdings, LLC; Date of Mailing: Aug. 10, 2021; 17 pages.

Extended European Search Report received for Application No. 21791938.0, Applicant: Shifamed Holdings, LLC; Date of Mailing: Apr. 3, 2024; 6 pages.

Ando et al., "Left ventricular decompression through a patent foramen ovale in a patient with hypertrophic cardiomyopathy: a case report," Cardiovascular Ultrasound volume, Article No. 2 (2004).

Braunwald, Heart Disease, Chapter 6, 2015, p. 186.

Bridges et al., "The Society of Thoracic Surgeons practice guideline series: transmyocardial laser revascularization," The Annals of Thoracic Surgery, vol. 77, Issue 4, Apr. 2004, pp. 1494-1502.

Bristow et al., "Improvement in cardiac myocyte function by biological effects of medical therapy: A new concept in the treatment of heart failure," European Heart Journal, vol. 16, Issue suppl. F, Jul. 1995, pp. 20-31.

Case et al., "Relief of High Left-Atrial Pressure in Left-Ventricular Failure," Lancet, Oct. 17, 1964, pp. 841-842.

Coats et al., "Controlled trial of physical training in chronic heart failure. Exercise performance, hemodynamics, ventilation, and autonomic function," Circulation, 1992;85:2119-2131.

Davies et al., "Reduced contraction and altered frequency response of isolated ventricular myocytes from patients with heart failure," Circulation, (1995), 92:2540-2549, Circulation, (1995), 92:2540-2549.

Ennezat et al., "An unusual case of low-flow, low gradient severe aortic stenosis: Left-to-right shunt due to atrial septal defect," Cardiology, (2009), 113(2):146-148.

Ewert et al., "Masked Left Ventricular Restriction in Elderly Patients With Atrial Septal Defects: A Contraindication for Closure," Catheterization and Cardiovascular Interventions, 52: 177-180, 2001.

Ewert et al., "Acute left heart failure after interventional occlusion of an atrial septal defect," Z. Kardiol., Catheterization and Cardiovascular Interventions, Z. Kardiol., (May 2001), 90(5):362-366.

Geiran et al., "Changes in cardiac dynamics by opening an interventricular shunt in dogs," J. Surg. Res., (Jan. 1990), 48(1):6-12.

Gelernter-Yaniv et al., "Transcatheter closure of left-to-right interatrial shunts to resolve hypoxemia," Congenit. Heart Dis., (Jan. 2008), 31(1):47-53.

Gewillig et al., "Creation with a stent of an unrestrictive lasting atrial communication," Cardio. Young, (2002), 12(4):404-407.

Khositseth et al., "Transcatheter Amplatzer Device Closure of Atrial Septal Defect and Patent Foramen Ovale in Patients With Presumed Paradoxical Embolism," Mayo Clinic Proc., 79:35-41 (2004).

Kramer et al., "Controlled study of captopril in chronic heart failure: A rest and exercise hemodynamic study," Circulation, (1983), 67(4):807-816.

Lai et al., "Bidirectional shunt through a residual atrial septal defect after percutaneous transvenous mitral commissurotomy," Cardiology, (1993), 83(3):205-207.

Lemmer et al., "Surgical implications of atrial septal defect complicating aortic balloon valvuloplasty," Ann. thorac. Surg., (Aug. 1989), 48(2):295-297.

Park et al., "Blade atrial septostomy: collaborative study," Circulation, 66(2):258-266 (1982).

Roven et al., "Effect of Compromising Right Ventricular Function in Left Ventricular Failure by Means of Interatrial and Other Shunts," American Journal Cardiology, 24:209-219 (1969).

(56) References Cited

OTHER PUBLICATIONS

Salehian et al., "Improvements in Cardiac Form and Function After Transcatheter Closure of Secundum Atrial Septal Defects," Journal of the American College of Cardiology, 45(4):499-504 (2005).

Schmitto et al., "Chronic heart failure induced by multiple sequential coronary microembolization in sheep," The International Journal of Artificial Organs, 31(4):348-353 (2008).

Schubert et al., "Left ventricular conditioning in the elderly patient to prevent congestive heart failure after transcatheter closure of the atrial septal defect," Catheter Cardiovasc. Interv., (2005), 64(3):333-337.

Stormer et al., "Comparative study of in vitro flow characteristics between a human aortic valve and a designed aortic and six corresponding types of prosthetic heart valves," European Surgical Research, (1976), 8(2):117-131.

Stumper et al., "Modified technique of stent fenestration of the atrial septum, Heart," (2003), 89:1227-1230.

Trainor et al., "Comparative Pathology of an Implantable Left Atrial Pressure Sensor." ASAIO Journal, Clinical Cardiovascular/Cardiopulmonary Bypass, 59(5):486-92 (2013).

Zhou et al., "Unidirectional valve patch for repair of cardiac septal defects with pulmonary hypertension," Annals of Thoracic Surgeons, 60: 1245-1249, 1995.

SYSTEMS AND METHODS FOR RADIOGRAPHIC MONITORING OF SHUNTS

CROSS-REFERENCE TO RELATED APPLICATION(S)

This application is a 35 U.S.C. § 371 U.S. National Phase application of International Patent Application No. PCT/US2021/028787, filed Apr. 23, 2021, which claims the benefit of U.S. Provisional Patent Application No. 63/014,318, filed Apr. 23, 2020, each of which is herein incorporated by reference in its entirety.

TECHNICAL FIELD

The present technology generally relates to implantable medical devices and, in various aspects, to methods for monitoring implantable interatrial systems for selectively controlling blood flow between cavities of a patient's heart.

BACKGROUND

Heart failure is a medical condition associated with the inability of the heart to effectively pump blood to the body. Heart failure affects millions of people worldwide, and may arise from multiple root causes, but is generally associated with myocardial stiffening, myocardial shape remodeling, and/or abnormal cardiovascular dynamics. Chronic heart failure is a progressive disease that worsens considerably over time. Initially, the body's autonomic nervous system adapts to heart failure by altering the sympathetic and parasympathetic balance. While these adaptations are helpful in the short-term, over a longer period of time they serve to make the disease worse.

Heart failure (HF) is a medical term that includes both heart failure with reduced ejection fraction (HFrEF) and heart failure with preserved ejection fraction (HFpEF). The prognosis with both HFpEF and HFrEF is poor; one-year mortality is 26% and 22%, respectively, according to one epidemiology study. In spite of the high prevalence of HFpEF, there remain limited options for HFpEF patients. Pharmacological therapies have been shown to impact mortality in HFrEF patients, but there are no similarly-effective evidence-based pharmacotherapies for treating HFpEF patients. Current practice is to manage and support patients while their health continues to decline. Moreover, people may live unknowingly with heart failure until treatment options are limited. For example, a patient with HFpEF may not be symptomatic until the heart failure disease has progressed to the late stages or the patient presents with comorbidities.

A common symptom among heart failure patients is elevated left atrial pressure. In the past, clinicians have treated patients with elevated left atrial pressure by creating a shunt between the left and right atria using a blade or balloon septostomy. The shunt decompresses the left atrium (LA) by relieving pressure to the right atrium (RA) and systemic veins. Over time, however, the shunt typically will close or reduce in diameter. More recently, percutaneous interatrial shunt devices have been developed which have been shown to effectively reduce left atrial pressure. However, these percutaneous devices generally have an annular passage with a fixed diameter which fails to account for a patient's changing physiology and condition. For this reason, existing percutaneous shunt devices may have a diminishing clinical effect after a period of time. Many existing percutaneous shunt devices typically are also only available in a single size that may work well for one patient but not another. Also, sometimes the amount of shunting created during the initial procedure is later determined to be less than optimal months after implantation. Accordingly, there is a need for improved devices, systems, and methods for treating heart failure patients, particularly those with elevated left atrial pressure.

DETAILED DESCRIPTION

The present technology is generally directed to systems and methods for monitoring interatrial shunting systems. A system configured in accordance with an embodiment of the present technology can include, for example, a shunting element implantable into a patient at or adjacent to a septal wall. The shunting element can include a lumen fluidly connecting cavities of the patient's heart (e.g., the LA and the RA) to facilitate blood flow therebetween. The geometry (e.g., size and/or shape) of the lumen can be selectively adjustable (e.g., non-invasively adjustable) to control the amount of blood flow therethrough.

In some embodiments, the shunting element includes one or more radiopaque elements associated with the lumen to allow for non-invasive monitoring of the lumen geometry. For example, to determine the size of the lumen (e.g., before, during, and/or after adjusting the lumen), the clinician can obtain radiographic images of the shunting element and the radiopaque elements from multiple viewing angles (e.g., orthogonal and/or orthonormal viewing angles). Subsequently, the size of the lumen can be calculated based on the locations of the radiopaque elements in the images, the locations of the radiopaque elements relative to the lumen, the viewing angles from which the images were taken, and/or scaling information for the images. The present technology is expected to improve treatment efficacy by allowing the clinician to monitor lumen geometry, determine whether lumen adjustments would be beneficial, and/or confirm whether lumen adjustments were successful.

The terminology used in the description presented below is intended to be interpreted in its broadest reasonable manner, even though it is being used in conjunction with a detailed description of certain specific embodiments of the present technology. Certain terms may even be emphasized below; however, any terminology intended to be interpreted in any restricted manner will be overtly and specifically defined as such in this Detailed Description section. Additionally, the present technology can include other embodiments that are within the scope of the examples but are not described in detail with respect to FIGS. 1-4D.

Reference throughout this specification to "one embodiment" or "an embodiment" means that a particular feature, structure, or characteristic described in connection with the embodiment is included in at least one embodiment of the present technology. Thus, the appearances of the phrases "in one embodiment" or "in an embodiment" in various places throughout this specification are not necessarily all referring to the same embodiment. Furthermore, the particular features or characteristics may be combined in any suitable manner in one or more embodiments.

Reference throughout this specification to relative terms such as, for example, "generally," "approximately," and "about" are used herein to mean the stated value plus or minus 10%.

As used herein, the terms "interatrial device," "interatrial shunt device," "IAD," "IASD," "interatrial shunt," and "shunt" are used interchangeably to refer to a device that, in at least one configuration, includes a shunting element that provides a blood flow between a first region (e.g., a LA of a heart) and a second region (e.g., a RA or coronary sinus of the heart) of a patient. Although described in terms of a shunt between the atria, namely the left and right atria, one will appreciate that the technology may be applied equally to devices positioned between other chambers and passages of the heart, or between other parts of the cardiovascular system or other system. For example, any of the shunts described herein, including those referred to as "interatrial," may be nevertheless used and/or modified to shunt between the LA and the coronary sinus, or between the right pulmonary vein and the superior vena cava. Moreover, while the disclosure herein primarily describes shunting blood from the LA to the RA, the present technology can be readily adapted to shunt blood from the RA to the LA to treat certain conditions, such as pulmonary hypertension. For example, mirror images of embodiments, or in some cases identical embodiments, used to shunt blood from the LA to the RA can be used to shunt blood from the RA to the LA in certain patients.

Although certain embodiments herein are described with respect to radiopaque elements configured to be visualized via radiographic imaging, it will be appreciated that the principles of the present technology can be adapted for use with other imaging methods. For example, the present technology can alternatively or additionally use markers with selective echogenicity (e.g., largely hyperechoic) configured to be visualized through ultrasound imaging and related imaging methods.

The headings provided herein are for convenience only and do not interpret the scope or meaning of the claimed present technology.

A. Interatrial Shunts for Treatment of Heart Failure

Heart failure can be classified into one of at least two categories based upon the ejection fraction a patient experiences: (1) HFpEF, historically referred to as diastolic heart failure or (2) HFrEF, historically referred to as systolic heart failure. One definition of HFrEF is a left ventricular ejection fraction lower than 35%-40%. Though related, the underlying pathophysiology and the treatment regimens for each heart failure classification may vary considerably. For example, while there are established pharmaceutical therapies that can help treat the symptoms of HFrEF, and at times slow or reverse the progression of the disease, there are limited available pharmaceutical therapies for HFpEF with only questionable efficacy.

In heart failure patients, abnormal function in the left ventricle (LV) leads to pressure build-up in the LA. This leads directly to higher pressures in the pulmonary venous system, which feeds the LA. Elevated pulmonary venous pressures push fluid out of capillaries and into the lungs. This fluid build-up leads to pulmonary congestion and many of the symptoms of heart failure, including shortness of breath and signs of exertion with even mild physical activity. Risk factors for HF include renal dysfunction, hypertension, hyperlipidemia, diabetes, smoking, obesity, old age, and obstructive sleep apnea. HF patients can have increased stiffness of the LV which causes a decrease in left ventricular relaxation during diastole resulting in increased pressure and inadequate filling of the ventricle. HF patients may also have an increased risk for atrial fibrillation and pulmonary hypertension, and typically have other comorbidities that can complicate treatment options.

Figure 1:
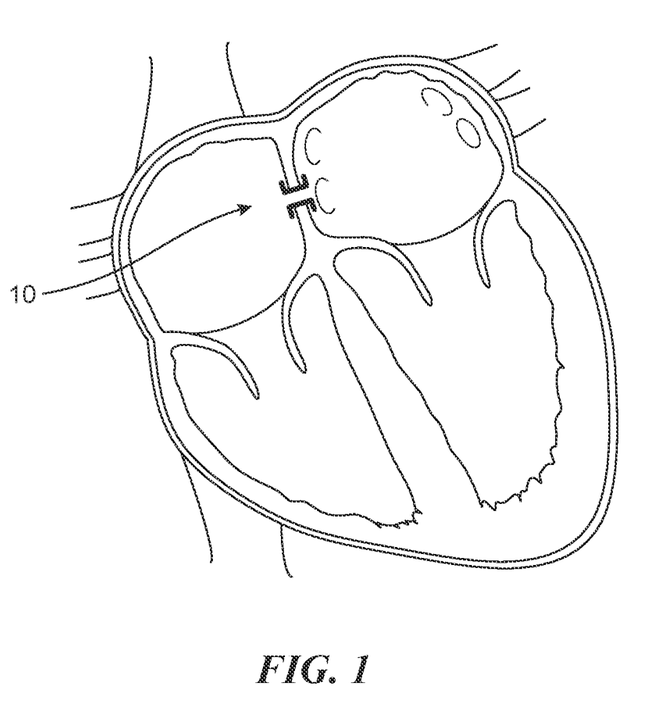
FIG. 1 is a schematic illustration of an interatrial device implanted in a heart and configured in accordance with an embodiment of the present technology.

Interatrial shunts have recently been proposed as a way to reduce elevated left atrial pressure, and this emerging class of cardiovascular therapeutic interventions has been demonstrated to have significant clinical promise. FIG. 1 shows the conventional placement of a shunt in the septal wall between the LA and RA. Most conventional interatrial shunts (e.g., shunt 10) involve creating a hole or inserting a structure with a lumen into the atrial septal wall, thereby creating a fluid communication pathway between the LA and the RA. As such, elevated left atrial pressure may be partially relieved by unloading the LA into the RA. In early clinical trials, this approach has been shown to improve symptoms of heart failure.

One challenge with many conventional interatrial shunts is determining the most appropriate size and shape of the shunt lumen. A lumen that is too small may not adequately unload the LA and relieve symptoms; a lumen that is too large may overload the RA and right heart more generally, creating new problems for the patient. Moreover, the relationship between pressure reduction and clinical outcomes and the degree of pressure reduction required for optimized outcomes is still not fully understood, in part because the pathophysiology for HFpEF (and to a lesser extent, HFrEF) is not completely understood. As such, clinicians are forced to take a best guess at selecting the appropriately sized shunt (based on limited clinical evidence) and generally cannot adjust the sizing over time. Worse, clinicians must select the size of the shunt based on general factors (e.g., the size of the patient's anatomical structures, the patient's hemodynamic measurements taken at one snapshot in time, etc.) and/or the design of available devices rather than the individual patient's health and anticipated response. With many such traditional devices, the clinician does not have the ability to adjust or titrate the therapy once the device is implanted, for example, in response to changing patient conditions such as progression of disease. By contrast, interatrial shunting systems configured in accordance with embodiments of the present technology allow a clinician to select shunt size—perioperatively or post-implant—based on the patient and, as discussed above, allow for non-invasive monitoring of lumen geometry to determine whether lumen adjustments would be beneficial and/or confirm whether lumen adjustments were successful.

B. Select Embodiments of Methods for Monitoring Interatrial Shunting Systems

As provided above, the present technology is generally directed to methods for monitoring interatrial shunting systems. Such systems include a shunting element implantable into a patient at or adjacent to a septal wall. The shunting element can include a lumen fluidly connecting the LA and the RA of the patient to facilitate blood flow therebetween. In some embodiments, the lumen is invasively or non-invasively adjustable to selectively control blood flow between the LA and the RA. To allow for monitoring of the lumen geometry (e.g., to confirm whether a desired adjustment was successfully achieved, determine whether an adjustment would be beneficial, etc.), the shunting element can include at least two radiopaque elements positioned such that the spatial relationship between the radiopaque elements varies based on the lumen geometry. Accordingly, the clinician can determine the lumen geometry by taking radiographic images of the radiopaque elements from different viewing angles and calculating the spatial relationship between the radiopaque elements from the image data.

Figure 2:
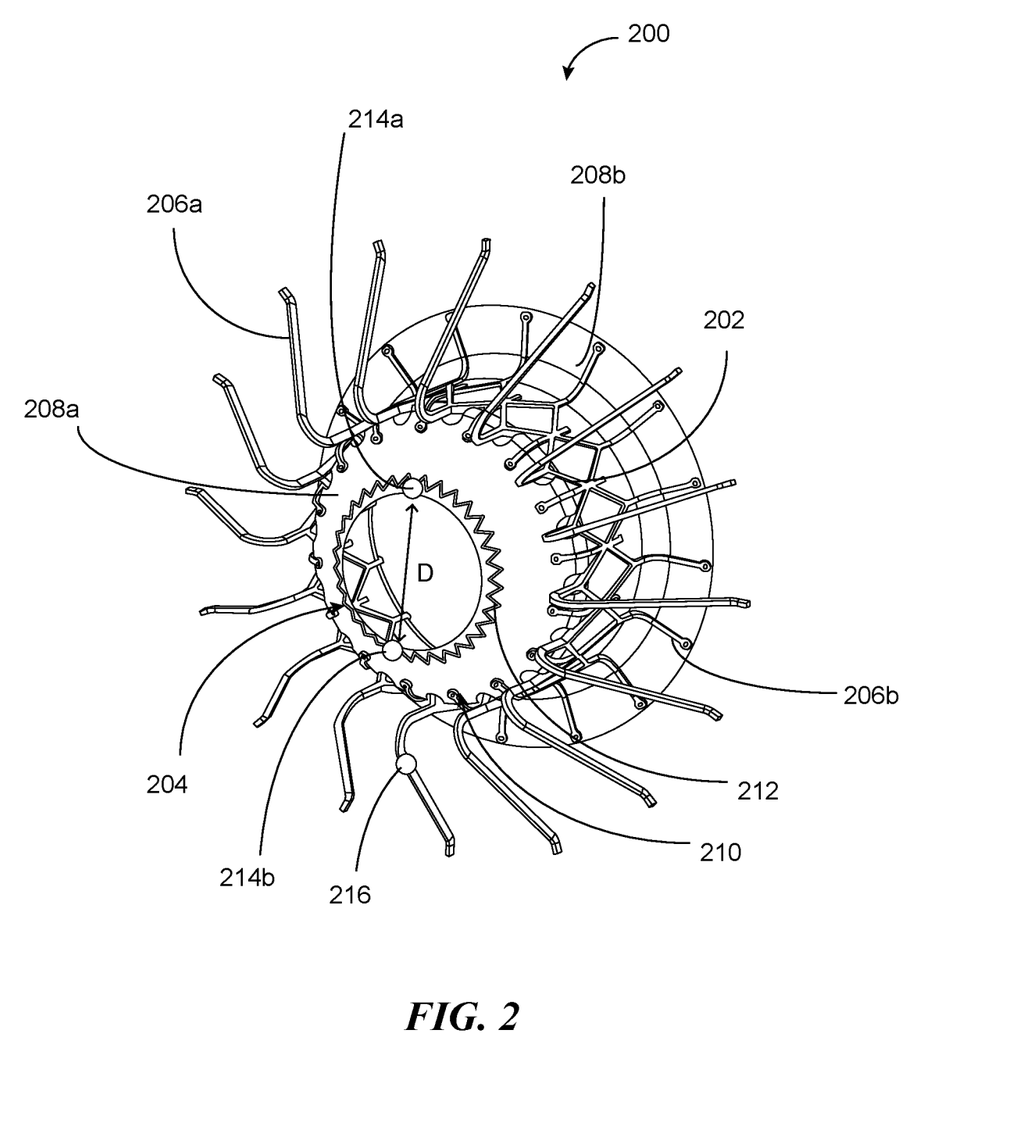
FIG. 2 is a perspective view of an interatrial shunting system configured in accordance with an embodiment of the present technology.

FIG. 2 is a perspective view of an interatrial shunting system 200 configured in accordance with an embodiment of the present technology. The system 200 includes a shunting element 202 defining a lumen 204 therethrough. When implanted in the septal wall (not shown) of a patient, the shunting element 202 can fluidly connect the LA (not shown) and the RA (not shown) via the lumen 204. In some embodiments, the geometry (e.g., size and/or shape) of the lumen 204 is adjustable (e.g., invasively or non-invasively adjustable) to alter the amount of fluid flow through the shunting element 202, as described in greater detail below.

The shunting element 202 can be secured to the septal wall via one or more first anchoring elements 206a and one or more second anchoring elements 206b. Anchoring elements 206a/206b may assume a variety of shapes, such as struts, flanges, coils, braids, cones, etc. In some embodiments, the first anchoring elements 206a are configured to engage a portion of the septal wall facing a first heart chamber (e.g., the RA) and the second anchoring elements 206b are configured to engage a portion of the septal wall facing a second heart chamber (e.g., the LA). In other embodiments the shunting element 202 is anchored in place using anchoring elements positioned on only one side of the septal wall. Optionally, a single anchoring element may be used on one or both sides of the septal wall. In yet other embodiments, the system 200 does not include first and second anchoring elements 206a-b and is instead secured in place by exerting a radially outward pressure against the septal wall or by other suitable mechanisms.

The system 200 can include a first membrane 208a and a second membrane 208b operably coupled to the shunting element 202 (e.g., carried by, connected to, and/or at least partially covering the shunting element 202). In the illustrated embodiment, for example, the first membrane 208a is connected to an end portion of the shunting element 202 near the lumen 204 and the first anchoring elements 206a, while the second membrane 208b is connected to the remaining portions of the shunting element 202 and to the second anchoring elements 206b. The membranes 208a-b can be flexible and can be made of a material that is impermeable to or otherwise resists blood flow therethrough. Optionally, the material can be an anti-thrombogenic material. In some embodiments, the membranes 208a-b are made of a thin, elastic material such as a polymer. For example, the membranes 208a-b can be made of polytetrafluoroethylene (PTFE), expanded PTFE (ePTFE), silicone, nylon, polyethylene terephthalate (PET), polyether block amide (pebax), polyurethane, blends or combinations of these materials, or other suitable materials. It will be appreciated that the first and second membranes 208a-b can be configured in many different ways. In other embodiments, for example, the first and second membranes 208a-b can be connected to different portions of the shunting element 202. In further embodiments, the first and second membranes 208a-b can be combined into a single unitary membrane. Optionally, one or both of the first and second membranes 208a-b can be omitted.

In some embodiments, the system 200 includes a flow control mechanism 210 configured to change a size, shape, and/or other characteristic of the shunting element 202 to selectively modulate the flow of fluid through the lumen 204. For example, the flow control mechanism 210 can be configured to selectively increase and/or decrease a size (e.g., diameter) of the lumen 204 in response to an input. In other embodiments, the flow control mechanism 210 is configured to otherwise affect the geometry (e.g., size and/or shape) or another characteristic of the lumen 204. In the illustrated embodiment, for example, the flow control mechanism 210 includes an annular structure 212 (e.g., a band, ring, frame, etc.) surrounding the lumen 204. The portions of the first membrane 208a around the perimeter of the lumen 204 can be coupled to the annular structure 212. As a result, the geometry of the lumen 204 can be altered directly or indirectly by adjusting the geometry of the annular structure 212 (e.g., by deforming, deflecting, or otherwise changing the annular structure 212 from a first configuration to a second configuration). The changes in the geometry of the annular structure 212 can deform (e.g., stretch, compress) or otherwise move the portions of the first membrane 208a surrounding the lumen 204 thereby altering the geometry of the lumen 204.

In some embodiments, the geometry of the annular structure 212 can be altered directly using mechanical techniques (e.g., dilating with a balloon). Alternatively or in combination, one or more portions of the annular structure 212 can be made of a shape memory material (e.g., nitinol). In such embodiments, for example, changes to the geometry of the annular structure 212 (and therefore the lumen 204) can be induced by applying external stresses to the annular structure 212 and/or by inducing internal stresses in the annular structure 212 via the application of energy (e.g., heating the annular structure 212 beyond a transition temperature that results in at least a temporary alteration of the material state).

Alternatively or in combination, the system 200 can include other types of flow control mechanisms configured to selectively change the geometry of the lumen 204. In some embodiments, for example, the flow control mechanism 210 can include one or more motors, such as electromagnetic motors, implanted battery and mechanical motors, MEMS motors, micro brushless DC motors, piezoelectric based motors, solenoids, and other motors. In other embodiments, the flow control mechanism 210 includes one or more shape memory elements. A shape memory element can be configured to change in shape (e.g., transform between a first configuration and a second configuration) in response to a stimulus (e.g., heat or mechanical loading) as is known to those of skill in the art. In embodiments of the present technology that utilize heat or another form of energy applied to a shape memory element or another component of the system 200, the energy/heat can be applied both invasively (e.g., via a catheter delivering laser, radiofrequency, or another form of energy, via an internal stored energy source such as a supercapacitor, etc.), non-invasively (e.g., using radiofrequency energy delivered by a transmitter outside of the body, by focused ultrasound, etc.), or through a combination of these methods.

The system 200 further includes a first radiopaque element 214a and a second radiopaque element 214b (shown schematically) carried by the shunting element 202. The radiopaque elements 214a-b can be made of any material having sufficient density to reduce or inhibit the transmission of X-rays or other forms of electromagnetic radiation so that the radiopaque elements 214a-b can be visualized using radiographic imaging techniques (e.g., X-ray imaging). For example, the radiopaque elements 214a-b can be made of a metal (e.g., tantalum, gold, platinum), a polymer, a composite, a dye, a contrast medium (e.g., barium sulfate), or any other suitable material known to those of skill in the art. In some embodiments, the system 200 may alternatively or in combination contain markers with selective echogenicity (e.g., largely hyperechoic) to enable visualization through ultrasonic and related imaging methods.

The geometry (e.g., size, shape) of the radiopaque elements 214a-b can be configured in many different ways. For example, the radiopaque elements 214a-b can be bands, markers, discs, rivets, fasteners, beads, bearings, or any other structure suitable for incorporation in the system 200. The shape of the radiopaque elements 214a-b can be selected to facilitate visualization in radiographic images. In some embodiments, for example, the radiopaque elements 214a-b each have a spherical, circular, or cylindrical shape so that at least one dimension (e.g., diameter) of the element is fixed and readily ascertainable even when imaged from different viewing angles (e.g., for determining scaling as described in greater detail below). Alternatively, the radiopaque elements 214a-b can have another shape (e.g., square, rectangular, triangular, elliptical, polygonal, curvilinear, etc.). In some embodiments, some or all of the radiopaque elements 214a-b can have different sizes and/or shapes so they can be distinguished from each other.

In some embodiments, some or all of the radiopaque elements 214a-b are coupled to another component of the system 200 via adhesives, fasteners, bonding, etc. In the illustrated embodiment, for example, the radiopaque elements 214a-b can be attached to one or more of the shunting element 202, anchoring elements 206a-b, membranes 208a-b, flow control mechanism 210, or annular structure 212. Alternatively or in combination, some or all of the radiopaque elements 214a-b can be integrally formed with or otherwise be a part of another component. For example, one or more portions of the first membrane 208a surrounding the lumen 204 can be made from or otherwise include a radiopaque material. Radiopaque materials can be incorporated in the components of the system 200 in many different ways, such as by coating, printing, impregnating, or other techniques known to those of skill in the art. Optionally, in some embodiments the radiopaque elements 214a-b are not discrete components, but instead are features of a continuous radiopaque component that can be distinguished from each other in images. For example, the annular structure 212 can be made from a radiopaque material and can include distinct features (e.g., peaks, rivets, points, etc.) that serve as the radiopaque elements 214a-b for purposes of the methods described herein.

The radiopaque elements 214a-b can be operably coupled to and/or associated with the lumen 204 such that changes in the geometry of the lumen 204 produce corresponding changes in the spatial relationship of the radiopaque elements 214a-b to each other. For example, the system 200 can include a structure at least partially surrounding the lumen 204 (e.g., a frame, stent, membrane, ring, band, etc.) such that changes in the geometry of the structure correlate to changes in the geometry of the lumen. The radiopaque elements 214a-b can be included in, coupled to, or otherwise associated with the structure so that changes in the geometry of the structure alter the positions of the radiopaque elements 214a-b in one or more dimensions. In the illustrated embodiment, for example, the radiopaque elements 214a-b are positioned at or near the perimeter of the lumen 204 (e.g., attached to or incorporated into the first membrane 208a). The radiopaque elements 214a-b can be at diametrically opposed locations relative to the lumen 204 such that the distance D between the radiopaque elements 214a-b corresponds directly to a dimension (e.g., a diameter) of the lumen 204. As a result, the dimension of the lumen 204 can be determined based on the spacing between the radiopaque elements 214a-b in radiographic images, as described in greater detail below.

Although FIG. 2 illustrates two radiopaque elements 214a-b, in other embodiments the system 200 can include a different number of radiopaque elements 214, such as one, three, four, five, or more. In embodiments where the system 200 includes a plurality of radiopaque elements 214, the radiopaque elements 214 can be distributed across different locations of the system 200 (e.g., coupled to or included in the shunting element 202, anchoring elements 206a-b, membranes 208a-b, flow control mechanism 210, annular structure 212, etc.). The radiopaque elements 214 can be spaced apart from each other in a defined and precise spatial relationship to allow the lumen geometry to be reconstructed from radiographic images of the radiopaque elements 214, as described further below. For example, three or more radiopaque elements 214 can be spaced around the perimeter of the lumen 204 (e.g., with paired elements at diametrically opposite locations). The use of multiple radiopaque elements 214 is expected to provide redundancy that improves the accuracy and precision of the measurement techniques described herein.

In some embodiments, the system 200 can optionally include one or more calibration elements 216. As described in detail below with respect to FIG. 3, the one or more calibration elements 216 can be used to calculate a scaling factor to more accurately and precisely measure a dimension between the radiopaque elements 241a-b. Although shown as positioned on a first anchoring element 206a, the calibration elements 216 can alternatively be positioned on other portions of the system 200, such as within a housing (not shown) that carries a power supply or other electronic components of the system 200. The calibration elements 216 can also be spaced apart from the system 200, and/or positioned external to the patient.

Figure 3:
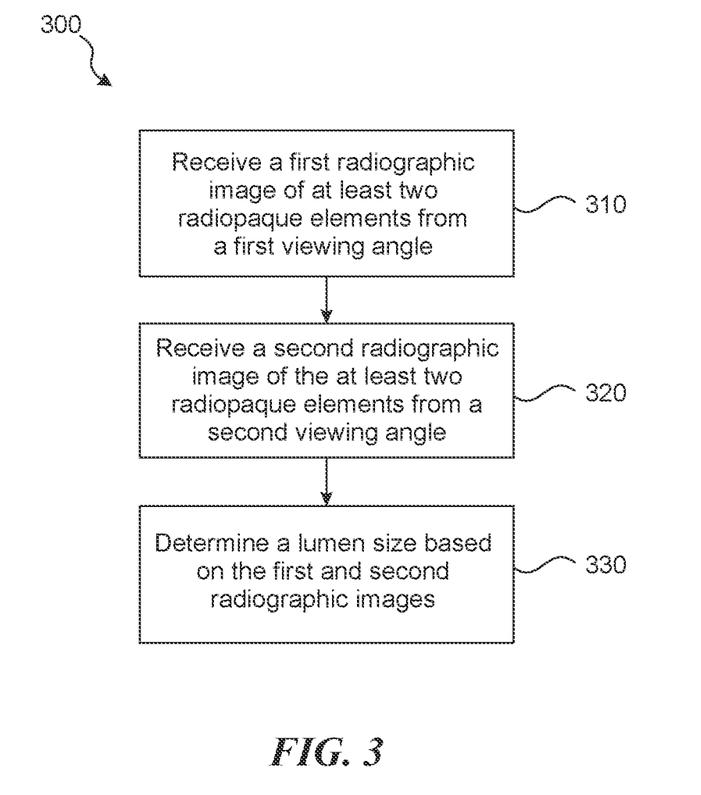
FIG. 3 is a block diagram illustrating a method for monitoring an interatrial shunting system configured in accordance with an embodiment of the present technology.

FIG. 3 is a block diagram illustrating a method 300 for monitoring an interatrial shunting system configured in accordance with an embodiment of the present technology. The method 300 can be applied to any interatrial shunting system including radiopaque elements, such as the system 200 described with respect to FIG. 2 or other suitable systems. In some embodiments, some or all of the steps of the method 300 are performed by a processor configured to execute instructions stored in a memory and/or a non-transitory computer-readable medium for performing the operations described herein. For example, the method 300 can be performed by a computing system configured to receive radiographic images and, based on the received images, determine a lumen size. In other embodiments, however, the method 300 may be implemented by other suitable mechanisms, systems, or devices.

Beginning at block 310, the method 300 includes receiving a first radiographic image of at least two radiopaque elements from a first viewing angle. The method continues with receiving a second radiographic image of the at least two radiopaque elements from a second viewing angle (block 320). The at least two radiopaque elements can be identical or generally similar to the radiopaque elements 214a-b described with respect to FIG. 2. For example, the radiopaque elements can be operably coupled to and/or associated with a lumen of the shunting element (e.g., positioned at or near the perimeter of the lumen). The radiopaque elements can have a specified spatial relationship with each other (e.g., diametrically opposite locations) that allows the lumen geometry to be reconstructed from the first and second radiographic images.

The first and second radiographic images can be any type of image data (e.g., still images, video) obtained via radiographic imaging techniques, such as an X-ray (e.g., a chest X-ray). Radiographic imaging techniques suitable for use with the embodiments herein include, but are not limited to, fluoroscopy (e.g., biplane fluoroscopy), C-arm X-ray imaging, and computed tomography (CT) imaging. In some embodiments, the first and second radiographic images are obtained by a suitable radiographic imaging device and transmitted to a computing device or system for subsequent processing and analysis. In embodiments of the system that include echogenic markers, the radiographic images may alternatively or in combination include ultrasonic images.

A radiographic imaging device can include at least one radiation source (e.g., an X-ray source) that is oriented relative to the patient's body to produce a radiographic image of the body along a corresponding viewing angle. In the method 300, the first radiographic image can be taken from a first viewing angle and the second radiographic image can be taken from a second viewing angle. The first and second viewing angles can be different viewing angles, e.g., the first viewing angle is a posterior-anterior viewing angle and the second viewing angle is a lateral viewing angle. In some embodiments, the first and second viewing angles are orthogonal or generally orthogonal such that they differ from each other by approximately 90 degrees. In some embodiments, the first and second viewing angles are orthonormal or generally orthonormal. In other embodiments the first and second viewing angles may not be orthogonal or orthonormal to each other.

The first and second radiographic images can be obtained in many different ways. For example, the first and second radiographic images can be taken by a radiographic imaging device having multiple radiation sources for taking images from multiple viewing angles (e.g., biplane fluoroscopy). In such embodiments, the first radiographic image can be obtained using a first radiation source oriented along the first viewing angle and the second radiographic image can be obtained using a second radiation source oriented along the second viewing angle. As another example, the first and second radiographic images can be taken by an imaging device having a single radiation source movable between a plurality of different orientations relative to the patient (e.g., a C-arm). In such embodiments, the first radiographic image can be obtained while the radiation source is oriented along the first viewing angle. The radiation source can then be moved to the second viewing angle to obtain the second radiographic image.

In some embodiments, the first and second radiographic images are obtained while the patient remains generally stationary. In such embodiments, radiographic images can be obtained by multiple radiation sources oriented along different viewing angles and/or by a single radiation source that is movable between different viewing angles. This approach is expected to improve the accuracy of capturing images at the desired viewing angles (e.g., orthonormal viewing angles). In other embodiments, however, the radiation source(s) can remain fixed while the patient is moved to different orientations. For example, the patient can be placed in a first orientation relative to the radiation source(s) to produce the first radiographic image, then subsequently moved to a second orientation to produce the second radiographic image.

In some embodiments, the first and second radiographic images are gated to reduce or prevent bodily movements of the patient (e.g., movements of the heart and/or lungs) from affecting measurement accuracy. For example, respiratory and/or cardiac movements can affect the position of the patient's body relative to the radiation source(s) as well as the position and geometry of implanted components (e.g., the shunting element, the lumen, the radiopaque elements). To limit the effect of these movements, the radiographic images can be gated based on the patient's respiratory cycle and/or cardiac cycle so that that the locations of the implanted components remain identical or generally similar across different images.

The method 300 further includes determining a lumen size based at least in part on the first and second radiographic images (block 330). In some embodiments, the first and second radiographic images each provide a two-dimensional (2D) projection of the three-dimensional (3D) locations of the radiopaque elements within the patient's body. Each radiographic image can be used to calculate various 2D measurements of the radiopaque elements. For example, the radiographic images can be used to calculate 2D locations or coordinates of each radiopaque element relative to a plane within a reference coordinate system (e.g., a coordinate system generally aligned with the patient's anatomical axes). The collective 2D measurements of the radiopaque elements in the images can be used to calculate the corresponding 3D spatial relationship of the radiopaque elements in the patient, which in turn is used to determine the geometry of the lumen (e.g., a lumen diameter). For example, in embodiments where a pair of radiopaque elements are positioned at diametrically opposed locations around the lumen perimeter, the 2D measurements can be used to calculate the 3D distance between the elements, which corresponds to a lumen diameter. Additional details of techniques for determining the lumen size are described with respect to FIGS. 4A-4D below.

In some embodiments, the method 300 also optionally includes calculating a scaling factor for converting 2D distances in the radiographic images (e.g., distances expressed in pixels) to actual 3D distances in the patient's body (e.g., distances expressed in mm). For example, to calculate the scaling factor, the sizes of the radiopaque elements in the radiographic images can be measured and compared to the known actual sizes of the radiopaque elements. Alternatively or in combination, the scaling factor can be calculated based on the size of at least one calibration element shown in the radiographic images. The calibration element(s) can have a spherical, circular, or cylindrical shape so that at least one dimension (e.g., diameter) of the calibration element(s) remains generally fixed when imaged from different viewing angles. In some embodiments, one or more calibration elements are located in the patient's body. For example, the calibration element(s) can be carried by the shunting element (e.g., the calibration element(s) 216 shown in FIG. 2, which may optionally be positioned within a housing of the system 200 for a power supply or other electronic components). In other embodiments, the calibration element(s) can be separate from but located near the shunting element, or can be located at a different region within the patient's body. In further embodiments, the calibration element(s) can be external to the patient's body (e.g., a ball bearing taped to the patient's body). The size of the calibration element(s) in the radiographic images can be measured and compared to the known actual size of the calibration element(s) to determine the scaling factor.

It will be appreciated that the method 300 can be implemented in many different ways. In some embodiments, for example, the method 300 further includes obtaining and/or receiving additional radiographic images of the radiopaque elements. For example, rather than taking a single radiographic image at each viewing angle, multiple images can be taken at each viewing angle, and the measurements from those images can be averaged or otherwise combined to improve accuracy. As another example, a third radiographic image can be obtained at a third viewing angle different from the first and second viewing angles and used to determine lumen size.

In some embodiments, the method 300 is performed before, during, and/or after a shunt adjustment operation. For example, a clinician can use the techniques described herein to non-invasively determine the lumen geometry of an implanted shunting element before making any adjustments to the shunting element, e.g., to assess the current state of the shunting element, determine whether the shunting element was implanted properly, evaluate whether adjustments would be beneficial, etc. The techniques herein can also be used for radiographic monitoring during a shunt adjustment procedure, e.g., to provide fluoroscopic guidance for invasive adjustments. Optionally, the techniques herein can also be used to measure the lumen geometry after the adjustment procedure has been completed, e.g., to confirm whether the intended adjustments were successfully achieved, assess whether additional adjustments would be beneficial, etc.

Optionally, the method 300 can be repeated multiple times to obtain radiographic images and determine the lumen size at multiple time points. For example, a first set of radiographic images can be obtained at a first time point to determine the lumen size at the first time point (e.g., before making an adjustment to a shunting element, during an initial phase of treatment, etc.). After a desired time period has passed (e.g., hours, days, weeks, months, years, etc.), a second set of radiographic images can be obtained at a second time point to determine the lumen size at the second time point (e.g., after making an adjustment to a shunting element, during a subsequent phase of treatment, etc.). This process can be repeated to determine the lumen size at as many additional time points as desired. The lumen sizes across the different time points can be compared to each other, e.g., to confirm whether an adjustment was successful, track the size of the lumen over time, detect whether undesirable changes in the lumen size have occurred. In some embodiments, the comparison of lumen sizes over time is used to evaluate the patient's condition (e.g., physiological state, health status, etc.).

Optionally, the measured lumen size can be compared to an estimated lumen size. In embodiments where adjustments to the shunting element are made via an implanted flow control mechanism (e.g., the flow control mechanism 210 of FIG. 2), the estimated lumen size can be calculated based at least partly on the configuration of the flow control mechanism (e.g., position, orientation, size, etc.). By comparing the measured and estimated lumen sizes, the clinician can assess whether the flow control mechanism was able to successfully adjust the shunting element and/or whether additional adjustments should be performed to achieve a desired lumen size. Optionally, the differences between the measured and estimated lumen sizes can be tracked and analyzed over time (e.g., via suitable software or other devices or techniques) to monitor and assess the condition of the patient and/or the shunting element.

Figure 4A:
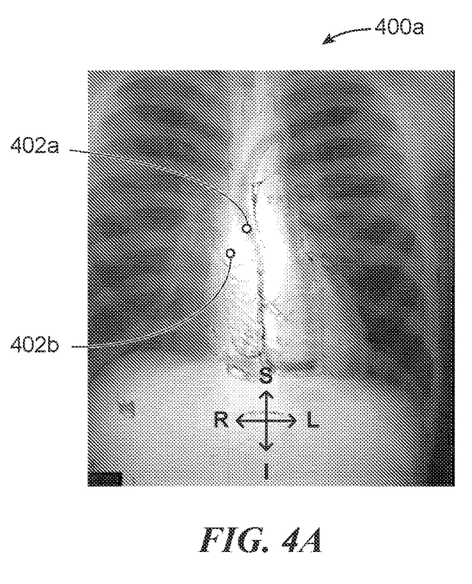
FIGS. 4A-4D illustrate calculation of lumen diameter from radiographic images in accordance with an embodiment of the present technology.
Figure 4B:
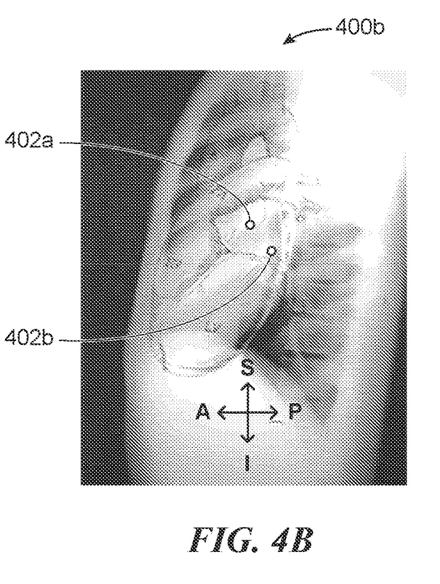
Figure 4C:
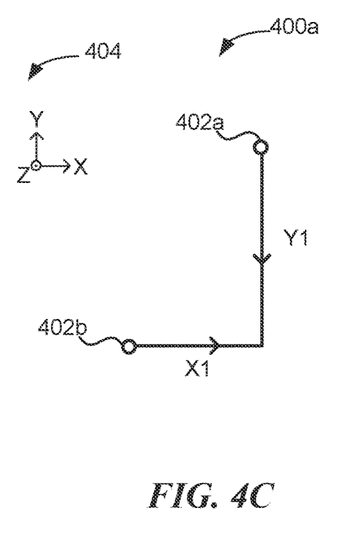
Figure 4D:
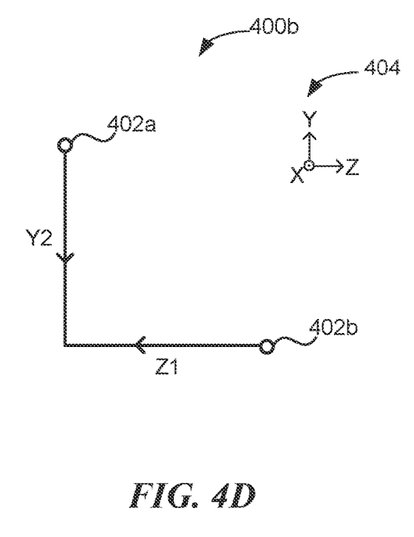

FIGS. 4A-4D illustrate calculation of lumen diameter from radiographic images in accordance with an embodiment of the present technology. More specifically, FIG. 4A illustrates a first radiographic image 400a of first and second radiopaque elements 402a-b, FIG. 4B illustrates a second radiographic image 400b of the radiopaque elements 402a-b, FIG. 4C illustrates 2D measurements of the radiopaque elements 402a-b in the first radiographic image 400a, and FIG. 4D illustrates 2D measurements of the radiopaque elements 402a-b in the second radiographic image 400b.

Referring first to FIGS. 4A and 4B together, the first radiographic image 400a includes image data of the two radiopaque elements 402a-b from a first viewing angle (e.g., a posterior-anterior viewing angle), and the second radiographic image 400b includes image data of the two radiopaque elements 402a-b from a second viewing angle orthonormal to the first viewing angle (e.g., a lateral viewing angle). The radiopaque elements 402a-b can be positioned at diametrically opposite locations near a perimeter of a lumen of a shunting element, as previously described. As can be seen in FIGS. 4A and 4B, the radiographic images 400a-b each provide a 2D projection of the 3D locations of the radiopaque elements 402a-b in the patient's body.

Referring next to FIGS. 4C and 4D together, the locations of the radiopaque elements 402a-b in the radiographic images 400a-b can be determined with respect to a reference coordinate system 404. The axes of the reference coordinate system 404 (e.g., x, y, z axes) can be configured to be generally aligned with the anatomical axes of the patient's body (e.g., left (L)-to-right (R), superior (S)-to-inferior (I), and anterior (A)-to-posterior (P) axes—shown in FIGS. 4A and 4B). In other embodiments, however, the reference coordinate system 404 can be aligned with other anatomical axes, or can be aligned with an off-axis imaging plane (e.g., right anterior oblique (RAO)-to-left anterior oblique (LAO)). In some embodiments, at least one axis of the reference coordinate system 404 is collinear with the axis of rotation between the first and second radiographic images 400a-b. In the illustrated embodiment, for example, the y-axis is collinear with the axis of rotation (e.g., the SI axis) and is coplanar with the patient's sagittal and coronal planes.

Referring to FIG. 4C, for the first radiographic image 400a, a line $Y_1$ can be drawn from the location of the first radiopaque element 402a in a direction parallel to the axis of rotation (e.g., parallel to the y-axis of the reference coordinate system 404 as indicated by the arrow along line $Y_1$). A line $X_1$ can be drawn from the second radiopaque element 402b in a direction perpendicular to line $Y_1$ (e.g., parallel to the x-axis of the reference coordinate system 404 as indicated by the arrow along line $X_1$). Lines $X_1$ and $Y_1$ can terminate at their point of intersection. The lengths of lines $X_1$ and $Y_1$ can provide a first set of 2D measurements for the radiopaque elements 402a-b.

Referring to FIG. 4D, for the second radiographic image 400b, a line $Y_2$ can be drawn from the location of the first radiopaque element 402a in a direction parallel to the axis of rotation (e.g., parallel to the y-axis of the reference coordinate system 404 as indicated by the arrow along line $Y_2$). A line $Z_1$ can be drawn from the second radiopaque element 402b in a direction perpendicular to line $Y_2$ (e.g., parallel to the z-axis of the reference coordinate system 404 as indicated by the arrow along line $Z_1$). Lines $Z_1$ and $Y_2$ can terminate at their point of intersection. The lengths of lines $Z_1$ and $Y_2$ can provide a second set of 2D measurements for the radiopaque elements 402a-b.

The 3D spatial relationship between the radiopaque elements 402a-b can be reconstructed based on the first and second sets of 2D measurements (e.g., $X_1$, $Y_1$, $Z_1$, $Y_2$). In the illustrated embodiment, $X_1$ corresponds to the x-distance between the radiopaque elements 402a-b, $Y_1$ and/or $Y_2$ correspond to the y-distance, and $Z_1$ corresponds to the z-distance. In some embodiments, either $Y_1$, $Y_2$, or both can be used to calculate the y-distance. As can be seen in FIGS. 4C and 4D, because lines $Y_1$ and $Y_2$ are parallel to the axis of rotation, the lengths of lines $Y_1$ and $Y_2$ are expected to be identical. However, $Y_1$ and $Y_2$ may not be identical if the first and second radiographic images 400a-b are not exactly orthonormal to each other, e.g., due to variations in patient posture, respiration, cardiac biomechanics, and/or the rotational precision of the imaging device. Accordingly, in some embodiments, $Y_1$ and $Y_2$ are averaged to improve the measurement accuracy. The 3D distance between the radiopaque elements 402a-b, D, which corresponds to the lumen diameter, can then be calculated using the following equation:

$$D = \sqrt{X_1^2 + Z_1^2 + \left(\frac{Y_1 + Y_2}{2}\right)^2}$$

Although FIGS. 4A-4D illustrate a lumen size calculation performed using two radiographic images 400a-b and two radiopaque elements 402a-b, one of skill in the art will appreciate that the principles described herein can be adapted for a different number of radiographic images and/or radiopaque elements. Moreover, although the calculation described with respect to FIGS. 4A-4D involves two radiopaque elements 402a-b positioned at diametrically opposed locations around the lumen, the present technology can be adapted for use with other arrangements of radiopaque elements relative to the lumen.

As one of skill in the art will appreciate from the disclosure herein, various features of the methods and systems described above can be omitted without deviating from the scope of the present technology. Likewise, additional features not explicitly described above may be added to the methods and systems without deviating from the scope of the present technology. Accordingly, the methods and systems described herein are not limited to those configurations expressly identified, but rather encompasses variations and alterations of the described methods and systems. Moreover, the following paragraphs provide additional description of various aspects of the present technology. One skilled in the art will appreciate that the following aspects can be incorporated into any of the methods and systems described above.

EXAMPLES

Several aspects of the present technology are set forth in the following examples:

1. A method for monitoring a shunting element implanted in a patient and having a lumen fluidly coupling a first body region of the patient and a second body region of the patient, the method comprising:
receiving a first radiographic image of at least two radiopaque elements associated with the lumen, wherein a spatial relationship between the at least two radiopaque elements varies according to a size of the lumen, and wherein the first radiographic image is taken from a first viewing angle;
receiving a second radiographic image of the at least two radiopaque elements, wherein the second radiographic image is taken from a second viewing angle different than the first viewing angle; and
determining the size of the lumen based, at least in part, on locations of the at least two radiopaque elements in the first and second radiographic images.

2. The method of example 1 wherein the second viewing angle is orthogonal to the first viewing angle.

3. The method of example 1 wherein the second viewing angle is orthonormal to the first viewing angle.

4. The method of any of examples 1-3 wherein the at least two radiopaque elements are positioned at or near a perimeter of the lumen.

5. The method of example 4 wherein the at least two radiopaque elements include a first radiopaque element and a second radiopaque element positioned at diametrically opposite locations at or near the perimeter of the lumen.

6. The method of example 4 wherein the at least two radiopaque elements include three or more radiopaque elements spaced around the perimeter of the lumen.

7. The method of any of examples 1-6 wherein the shunting element includes a structure at least partially surrounding the lumen, and wherein the structure includes the at least two radiopaque elements.

8. The method of example 7 wherein the structure comprises one or more of a frame, a stent, a membrane, a ring, or a band.

9. The method of any of examples 1-8 wherein the at least two radiopaque elements comprise bands, markers, discs, rivets, fasteners, or beads.

10. The method of any of examples 1-9 wherein the at least two radiopaque elements each have a spherical, cylindrical, or circular shape.

11. The method of any of examples 1-10 wherein:
the first and second radiographic images each include image data of at least one calibration element having a spherical, cylindrical, or circular shape; and
the method further comprises determining a scaling factor for the first and second radiographic images based at least in part on the image data of the at least one calibration element.

12. The method of example 11 wherein the at least one calibration element is carried by the shunting element.

13. The method of example 11 wherein the at least one calibration element is external to the patient's body.

14. The method of any of examples 1-13 wherein:
the first radiographic image is obtained using a first radiation source oriented along the first viewing angle; and
the second radiographic image is obtained using a second radiation source oriented along the second viewing angle.

15. The method of any of examples 1-13 wherein:
the first and second radiographic images are obtained using a single radiation source; and
the method further comprises moving the single radiation source between the first and second viewing angles to obtain the first and second radiographic images.

16. The method of any of examples 1-15 wherein:
the first radiographic image is obtained when the patient is positioned at a first orientation corresponding to the first viewing angle;
the second radiographic image is obtained using when the patient is positioned at a second orientation corresponding to the second viewing angle; and
the method further comprises moving the patient between the first and second orientations to obtain the first and second radiographic images.

17. The method of any of examples 1-16 wherein the first viewing angle is an anterior-posterior viewing angle and the second viewing angle is a lateral viewing angle.

18. The method of any of examples 1-17, further comprising:
receiving a third radiographic image of the at least two radiopaque elements, wherein the third radiographic image is taken at a third viewing angle different from the first and second viewing angles; and
determining the size of the lumen based at least in part on locations of the at least two radiopaque elements in the third radiographic image.

19. The method of any of examples 1-18 wherein the first and second radiographic images are gated based on one or more of a respiratory cycle or a cardiac cycle of the patient.

20. The method of any of examples 1-19 wherein determining the size of the lumen comprises:
determining two-dimensional measurements of the at least two radiopaque elements in each of the first and second radiographic images; and
calculating a three-dimensional distance between the at least two radiopaque elements based on the two-dimensional measurements.

21. The method of any of examples 1-20 wherein the first and second radiographic images are X-ray images.

22. The method of any of examples 1-21 wherein the lumen of the shunting element is selectively adjustable to control fluid flow therethrough.

23. The method of example 22, further comprising adjusting the lumen of the shunting element before, during, and/or after obtaining the first and second radiographic images.

24. The method of any of examples 1-23 wherein the first body region includes a first cavity of a heart of the patient and the second body region includes a second cavity of the heart of the patient, and wherein the first and second cavities of the heart of the patient include: (a) a left atrium and a right atrium, (b) a left ventricle and a right ventricle, or (c) a coronary sinus and the left ventricle.

25. The method of any of examples 1-24 wherein:
the first and second radiographic images are obtained at a first time point;
the size of the lumen is a first size; and
the method further comprises:
receiving one or more additional radiographic images of the at least two radiopaque elements obtained at a second time point different from the first time point; and
determining a second size of the lumen based, at least in part, on locations of the at least two radiopaque elements in the one or more additional radiographic images.

26. The method of example 25, further comprising comparing the first and second lumen sizes.

27. The method of example 26, further comprising evaluating one or more of a physiological state or health status of the patient based, at least in part, on the comparison of the first and second lumen sizes.

28. A system for monitoring a shunting element implanted in a patient and having a lumen fluidly coupling a first body region of the patient and a second body region of the patient, the system comprising:
a processor; and
a memory storing instructions that, when executed by the processor, cause the system to perform operations comprising:
receiving first radiographic image data of at least two radiopaque elements associated with the lumen, wherein a spatial relationship between the at least two radiopaque elements varies according to a size of the lumen, and wherein the first radiographic image data is taken from a first viewing angle;
receiving second radiographic image data of the at least two radiopaque elements, wherein the second radiographic image data is taken from a second viewing angle different than the first viewing angle; and
determining the size of the lumen based, at least in part, on locations of the at least two radiopaque elements in the first and second radiographic image data.

29. The system of example 28, further comprising a radiographic imaging device configured to obtain the first and second radiographic image data.

30. The system of example 28 or 29 wherein the second viewing angle is orthogonal to the first viewing angle.

31. The system of example 28 or 29 wherein the second viewing angle is orthonormal to the first viewing angle.

32. The system of any of examples 28-31 wherein the first body region includes a first cavity of a heart of the patient and the second body region includes a second cavity of the heart of the patient, and wherein the first and second cavities of the heart of the patient include: (a) a left atrium and a right atrium, (b) a left ventricle and a right ventricle, or (c) a coronary sinus and the left ventricle.

33. A non-transitory computer-readable medium storing instructions that, when executed by a processor of a system for monitoring a shunting element implanted in a patient and having a lumen fluidly coupling a first body region of the patient and a second body region of the patient, cause the system to perform operations comprising:
receiving first radiographic image data of at least two radiopaque elements associated with the lumen, wherein a spatial relationship between the at least two radiopaque elements varies according to a size of the lumen, and wherein the first radiographic image data is taken from a first viewing angle;
receiving second radiographic image data of the at least two radiopaque elements, wherein the second radiographic image data is taken from a second viewing angle different than the first viewing angle; and
determining the size of the lumen based, at least in part, on locations of the at least two radiopaque elements in the first and second radiographic image data.

34. The non-transitory computer-readable medium of example 33 wherein the second viewing angle is orthogonal to the first viewing angle.

35. The non-transitory computer-readable medium of example 33 wherein the second viewing angle is orthonormal to the first viewing angle.

36. The non-transitory computer-readable medium of any of examples 33-35 wherein the first body region includes a first cavity of a heart of a patient and the second body region includes a second cavity of a heart of the patient, and wherein the first and second cavities of the heart of the patient include: (a) a left atrium and a right atrium, (b) a left ventricle and a right ventricle, or (c) a coronary sinus and the left ventricle.

CONCLUSION

Embodiments of the present disclosure may include some or all of the following components: a battery, supercapacitor, or other suitable power source; a microcontroller, FPGA, ASIC, or other programmable component or system capable of storing and executing software and/or firmware that drives operation of an implant; memory such as RAM or ROM to store data and/or software/firmware associated with an implant and/or its operation; wireless communication hardware such as an antenna system configured to transmit via Bluetooth, WiFi, or other protocols known in the art; energy harvesting means, for example a coil or antenna which is capable of receiving and/or reading an externally-provided signal which may be used to power the device, charge a battery, initiate a reading from a sensor, or for other purposes. Embodiments may also include one or more sensors, such as pressure sensors, impedance sensors, accelerometers, force/strain sensors, temperature sensors, flow sensors, optical sensors, cameras, microphones or other acoustic sensors, ultrasonic sensors, ECG or other cardiac rhythm sensors, SpO2 and other sensors adapted to measure tissue and/or blood gas levels, blood volume sensors, and other sensors known to those who are skilled in the art. Embodiments may include portions that are radiopaque and/or ultrasonically reflective to facilitate image-guided implantation or image guided procedures using techniques such as fluoroscopy, ultrasonography, or other imaging methods. Embodiments of the system may include specialized delivery catheters/systems that are adapted to deliver an implant and/or carry out a procedure. Systems may include components such as guidewires, sheaths, dilators, and multiple delivery catheters. Components may be exchanged via over-the-wire, rapid exchange, combination, or other approaches.

Embodiments of the present disclosure may be implemented as computer-executable instructions, such as routines executed by a general-purpose computer, a personal computer, a server, or other computing system. The present technology can also be embodied in a special purpose computer or data processor that is specifically programmed, configured, or constructed to perform one or more of the computer-executable instructions explained in detail herein. The terms "computer" and "computing device," as used generally herein, refer to devices that have a processor and non-transitory memory, as well as any data processor or any device capable of communicating with a network. Data processors include programmable general-purpose or special-purpose microprocessors, programmable controllers, ASICs, programming logic devices (PLDs), or the like, or a combination of such devices. Computer-executable instructions may be stored in memory, such as RAM, ROM, flash memory, or the like, or a combination of such components. Computer-executable instructions may also be stored in one or more storage devices, such as magnetic or optical-based disks, flash memory devices, or any other type of non-volatile storage medium or non-transitory medium for data. Computer-executable instructions may include one or more program modules, which include routines, programs, objects, components, data structures, and so on that perform particular tasks or implement particular abstract data types.

The above detailed description of embodiments of the technology are not intended to be exhaustive or to limit the technology to the precise forms disclosed above. Although specific embodiments of, and examples for, the technology are described above for illustrative purposes, various equivalent modifications are possible within the scope of the technology as those skilled in the relevant art will recognize. For example, although steps are presented in a given order, alternative embodiments may perform steps in a different order. The various embodiments described herein may also be combined to provide further embodiments. For example, although this disclosure has been written to describe devices that are generally described as being used to create a path of fluid communication between the LA and RA, the LV and the right ventricle (RV), or the LA and the coronary sinus, it should be appreciated that similar embodiments could be utilized for shunts between other chambers of heart or for shunts in other regions of the body.

From the foregoing, it will be appreciated that specific embodiments of the technology have been described herein for purposes of illustration, but well-known structures and functions have not been shown or described in detail to avoid unnecessarily obscuring the description of the embodiments of the technology. Where the context permits, singular or plural terms may also include the plural or singular term, respectively.

Unless the context clearly requires otherwise, throughout the description and the examples, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof, means any connection or coupling, either direct or indirect, between two or more elements; the coupling of connection between the elements can be physical, logical, or a combination thereof. Additionally, the words "herein," "above," "below," and words of similar import, when used in this application, shall refer to this application as a whole and not to any particular portions of this application. Where the context permits, words in the above Detailed Description using the singular or plural number may also include the plural or singular number respectively. As used herein, the phrase "and/or" as in "A and/or B" refers to A alone, B alone, and A and B. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with some embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A method for monitoring a shunting element implanted in a patient and having a lumen fluidly coupling a first body region of the patient and a second body region of the patient, wherein the lumen of the shunting element is selectively adjustable to control fluid flow therethrough, the method comprising:
    receiving a first radiographic image of at least two radiopaque elements associated with the lumen, wherein a spatial relationship between the at least two radiopaque elements varies according to a size of the lumen, and wherein the first radiographic image is taken from a first viewing angle;
    receiving a second radiographic image of the at least two radiopaque elements, wherein the second radiographic image is taken from a second viewing angle different than the first viewing angle; and
    determining the size of the lumen based, at least in part, on locations of the at least two radiopaque elements in the first and second radiographic images.

2. The method of claim 1 wherein the second viewing angle is orthogonal to the first viewing angle.

3. The method of claim 1 wherein the second viewing angle is orthonormal to the first viewing angle.

4. The method of claim 1 wherein the at least two radiopaque elements are positioned at or near a perimeter of the lumen.

5. The method of claim 4 wherein the at least two radiopaque elements include a first radiopaque element and a second radiopaque element positioned at diametrically opposite locations at or near the perimeter of the lumen.

6. The method of claim 1 wherein the shunting element includes a structure at least partially surrounding the lumen, wherein the structure comprises one or more of a frame, a stent, a membrane, a ring, or a band, and wherein the structure includes the at least two radiopaque elements.

7. The method of claim 1 wherein the at least two radiopaque elements comprise bands, markers, discs, rivets, fasteners, or beads.

8. The method of claim 1 wherein the at least two radiopaque elements each have a spherical, cylindrical, or circular shape.

9. The method of claim 1 wherein:
the first and second radiographic images each include image data of at least one calibration element having a spherical, cylindrical, or circular shape; and
the method further comprises determining a scaling factor for the first and second radiographic images based at least in part on the image data of the at least one calibration element.

10. The method of claim 9 wherein the at least one calibration element is carried by the shunting element.

11. The method of claim 9 wherein the at least one calibration element is external to the patient's body.

12. The method of claim 1 wherein the first viewing angle is an anterior-posterior viewing angle and the second viewing angle is a lateral viewing angle.

13. The method of claim 1 wherein the first and second radiographic images are gated based on one or more of a respiratory cycle or a cardiac cycle of the patient.

14. The method of claim 1 wherein determining the size of the lumen comprises:
determining two-dimensional measurements of the at least two radiopaque elements in each of the first and second radiographic images; and
calculating a three-dimensional distance between the at least two radiopaque elements based on the two-dimensional measurements.

15. The method of claim 1, further comprising adjusting the lumen of the shunting element before, during, and/or after obtaining the first and second radiographic images.

16. The method of claim 1 wherein the first body region includes a first cavity of a heart of the patient and the second body region includes a second cavity of the heart of the patient, and wherein the first and second cavities of the heart of the patient include: (a) a left atrium and a right atrium, (b) a left ventricle and a right ventricle, or (c) a coronary sinus and the left ventricle.

17. A system for monitoring a shunting element implanted in a patient and having a lumen fluidly coupling a first body region of the patient and a second body region of the patient, the system comprising:
a processor; and
a memory storing instructions that, when executed by the processor, cause the system to perform operations comprising:
receiving first radiographic image data of at least two radiopaque elements associated with the lumen, wherein a spatial relationship between the at least two radiopaque elements varies according to a size of the lumen, wherein the lumen of the shunting element is selectively adjustable to control fluid flow therethrough, and wherein the first radiographic image data is taken from a first viewing angle;
receiving second radiographic image data of the at least two radiopaque elements, wherein the second radiographic image data is taken from a second viewing angle different than the first viewing angle; and
determining the size of the lumen based, at least in part, on locations of the at least two radiopaque elements in the first and second radiographic image data.

18. The system of claim 17 wherein the second viewing angle is orthogonal to the first viewing angle.

19. The system of claim 17 wherein the second viewing angle is orthonormal to the first viewing angle.

20. A non-transitory computer-readable medium storing instructions that, when executed by a processor of a system for monitoring a shunting element implanted in a patient and having a lumen fluidly coupling a first body region of the patient and a second body region of the patient, cause the system to perform operations comprising:
receiving first radiographic image data of at least two radiopaque elements associated with the lumen, wherein a spatial relationship between the at least two radiopaque elements varies according to a size of the lumen, wherein the lumen of the shunting element is selectively adjustable to control fluid flow therethrough, and wherein the first radiographic image data is taken from a first viewing angle;
receiving second radiographic image data of the at least two radiopaque elements, wherein the second radiographic image data is taken from a second viewing angle different than the first viewing angle; and
determining the size of the lumen based, at least in part, on locations of the at least two radiopaque elements in the first and second radiographic image data.

21. The non-transitory computer-readable medium of claim 20 wherein the second viewing angle is orthogonal to the first viewing angle.

22. The non-transitory computer-readable medium of claim 20 wherein the second viewing angle is orthonormal to the first viewing angle.

* * * * *